(12) United States Patent
Rasmussen

(10) Patent No.: US 7,268,466 B2
(45) Date of Patent: Sep. 11, 2007

(54) PIEZO ELECTRIC PUMP AND DEVICE WITH SUCH PUMP

(76) Inventor: Steen Brabrand Rasmussen, Birkholmvej 1, DK-3540, Lynge (DK)

( * ) Notice: Subject to any disclaimer, the term of this patent is extended or adjusted under 35 U.S.C. 154(b) by 51 days.

(21) Appl. No.: 10/501,224

(22) PCT Filed: Jan. 9, 2003

(86) PCT No.: PCT/DK03/00011

§ 371 (c)(1),
(2), (4) Date: Jul. 18, 2005

(87) PCT Pub. No.: WO03/058067

PCT Pub. Date: Jul. 17, 2003

(65) Prior Publication Data

US 2006/0197412 A1    Sep. 7, 2006

(30) Foreign Application Priority Data

Jan. 10, 2002    (DK) ............................... 2002 00038

(51) Int. Cl.
*H01L 41/08* (2006.01)
(52) U.S. Cl. .................... 310/328; 310/331; 128/746; 417/413.2
(58) Field of Classification Search .................. 310/328
See application file for complete search history.

(56) References Cited

U.S. PATENT DOCUMENTS

| 4,011,474 | A | * | 3/1977 | O'Neill ..................... 310/328 |
| 4,175,587 | A | | 11/1979 | Chadwick et al. |
| 4,231,287 | A | * | 11/1980 | Smiley ........................... 92/94 |
| 4,237,905 | A | | 12/1980 | Keller et al. |
| 4,688,582 | A | * | 8/1987 | Heller et al. ................ 600/559 |
| 5,063,946 | A | | 11/1991 | Wada |
| 5,798,600 | A | | 8/1998 | Sager et al. |
| 6,071,088 | A | | 6/2000 | Bishop et al. |
| 6,164,933 | A | | 12/2000 | Tani et al. |
| 6,869,275 | B2 | * | 3/2005 | Dante et al. ............. 417/413.2 |
| 7,011,507 | B2 | * | 3/2006 | Seto et al. .................. 417/412 |

FOREIGN PATENT DOCUMENTS

| EP | 0379719 | 8/1990 |
| WO | 8707218 | 12/1987 |

OTHER PUBLICATIONS

English Abstract of SU901659, Jan. 1982, of RYU Bansevichy et al. entitled "Vibratory Pump".

* cited by examiner

*Primary Examiner*—Mark Budd
(74) *Attorney, Agent, or Firm*—Dykema Gossett PLLC

(57) ABSTRACT

A measuring device for measuring in an ear canal includes a probe for insertion into an ear canal having an opening for letting air in to and out of the ear canal, and a pump for providing a pressure above a surrounding atmospheric pressure or below the surrounding atmospheric pressure, the pump including a housing with openings for inlet and/or outlet, where within the housing a piston element having piezo electric properties is disposed, one opening in the pump being operatively connected to the opening in the probe.

5 Claims, 2 Drawing Sheets

PIEZO ELECTRIC PUMP AND DEVICE WITH SUCH PUMP

AREA OF THE INVENTION

The invention relates to pumps incorporating a piezo electric pump element. The invention further relates to a device implementing a pump using the principles of the pump element having piezo electric properties for generating pressure differences.

BACKGROUND OF THE INVENTION

In audiological equipment a pump is in most cases provided for establishing a pressure difference in the ear canal in relation to the existing atmospheric pressure. This comprises both pressure levels above and below the existing atmospheric pressure. Such pressure difference is, e.g., created in connection with acoustic measurement in the ear canal in order to determine whether fluid is present in the middle ear, e.g., in connection with Otitis Media (middle ear inflammation).

The audiological equipment commercially available all suffer from the drawback that the pump types used in these are both bulky and in long-term use also unreliable. The size issue leads to instruments that are difficult to handle and the reliability issue leads to mechanical failure and malfunction with unnecessary repair and maintenance costs as well as patient re-examinations as the consequence.

There is for these reasons a need for improvement in the audiological equipment and the pumps finding use in this equipment.

A first objective of the present invention is to provide a measuring device for measurement in the ear canal which has a more reliable function, especially in long-term use.

A second objective is to provide a pump which is suitable for use in a measuring device for measurement in the ear canal.

SUMMARY OF THE INVENTION

According to the invention the first objective is achieved by means of a measuring device which includes a probe for insertion into an ear canal in a sealing manner and having an opening for transport of air into or out of the ear canal, and a pump for providing a pressure difference in relation to a surrounding atmospheric pressure, the pump including a housing with openings for inlet and/or outlet, where within the housing a piston element having a piezo electric properties is disposed, one opening in the pump being operatively connected to the opening in the probe.

The invention will provide a device with a more reliable function and hence reduce the before mentioned drawbacks significantly.

In a preferred embodiment valve elements are provided in connection to the inlet opening and the outlet opening for controlling the inlet and the outlet and where the valve elements have piezo electric properties. This enable the pump to operate at relatively high frequency rates compared to conventional valves.

In a further preferred embodiment the pump is adapted to operate at a frequency above 18 kHz, preferably above 20 kHz. Hereby the operation can take place at a frequency above the normal audible frequency range and hence a more comfortable test may be carried out.

In order to provide an increased safety a pressure operated passive valve element may be provided in connection with the pressurized parts of the device. It is obvious that a to high or to low pressure may have a damaging effect on the patients tympanic membrane and hence may cause hearing damage. The independent safety valve is therefore highly desired and in most cases a required element.

According to the invention, the second objective is achieved by means of a pump which includes a housing with an inlet opening and an outlet opening and a piston element having piezo electric properties in the housing, and valve elements in the inlet opening and the outlet opening valve for controlling the inlet and outlet, the valve elements having piezo electric properties.

This aspect of the invention will provide a pump with a more reliable function and hence reduce the before mentioned drawbacks significantly in connection with a device according to the invention and further provide similar advantages in other applications.

By incorporating the valve elements as defined the pump will have the ability of operating at significantly higher frequencies than such pumps normally are capable of doing. This means that a number of applications are in reach, which hitherto have not been accessible.

The pump may in a preferred embodiment be adapted to operate at a frequency above 18 kHz, preferably above 20 kHz.

DESCRIPTION OF A PREFERRED EMBODIMENT

Figure 1:
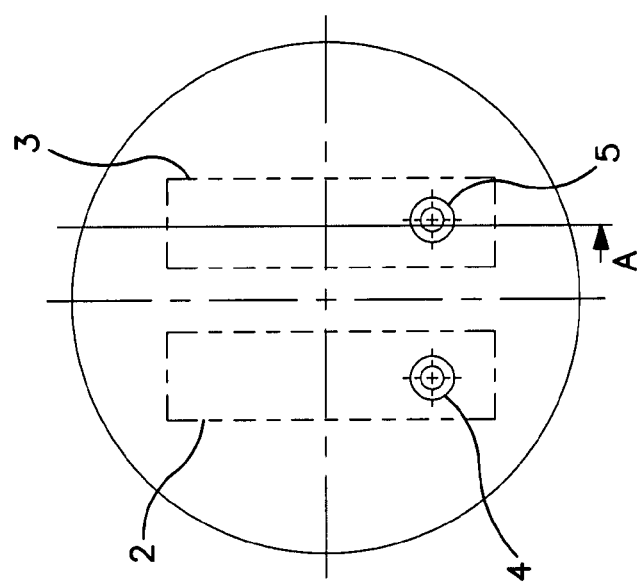
FIG. 1 is a schematic drawing showing the pump according to the invention in a top view.

Referring to FIG. 1 the pump according to the invention comprises a housing 7, 8 with opening 4 and opening 5. Valve elements 2,3 are indicated as located within the housing and intended for opening and closing the opening 4 and the opening 5, respectively.

Figure 2:
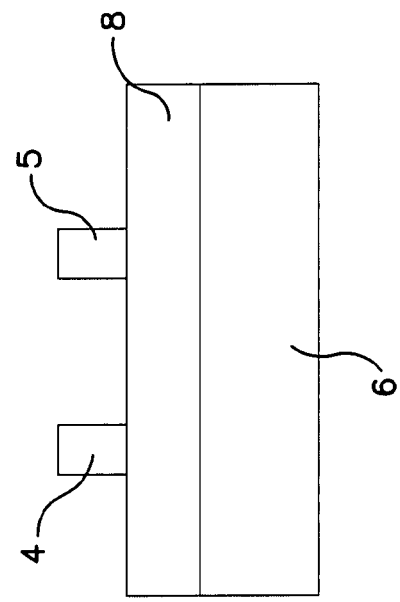
FIG. 2 is a schematic drawing showing the pump in FIG. 1 in a side view.

From FIG. 2 it appears that the openings 4 and 5 in the housing 7,8 are running through a pipe stub extending from the housing. This facilitates the connection of necessary tube elements.

Figure 3:
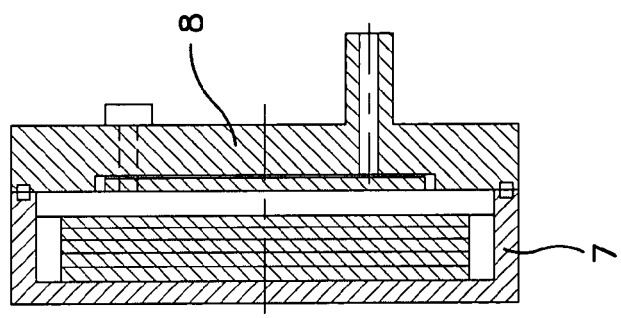
FIG. 3 is a schematic drawing showing the pump in FIG. 1 in a sectional view along the line A in FIG. 1

From FIG. 3 the inner cavity of the pump housing 7,8 appears. The two housing parts 7,8 are sealed along the circumferential edge. In the top part 8 an opening 5 pipe stub is located. On the side facing the housing inner cavity in the assembled state the two valve elements 2,3 are fastened. The valves can in principle be provided at any location, e.g. on the outside of the housing or within the passage where the opening and closing that need to be controlled. The valve elements each consist of a piezo electric element.

Each valve element is fastened at a location in a distance from the openings 4 and 5 in such a manner that the valve is closing an opening in one state of electrical influence, e.g. zero influence, and opening the same in another state of electrical influence. The valve is hereby of a type having piezo electrical properties that provide a bending of the valve element upon applying a certain electrical influence to it. In general the valve could have piezo electrical properties that provide any change in the physical dimensions, i.e. a bending of the valve element upon applying a certain electrical influence to it is one preferred embodiment. In the lower housing part 7 one or a series of piezo electrical elements are located in a stacked configuration so as to provide a piston element in the pump housing. Between the piston element and the inner sides of the housing element 7 an elastic yielding sealing is provided. This sealing may be a rubber O-ring or a silicone material or a similar substance.

Figure 4:
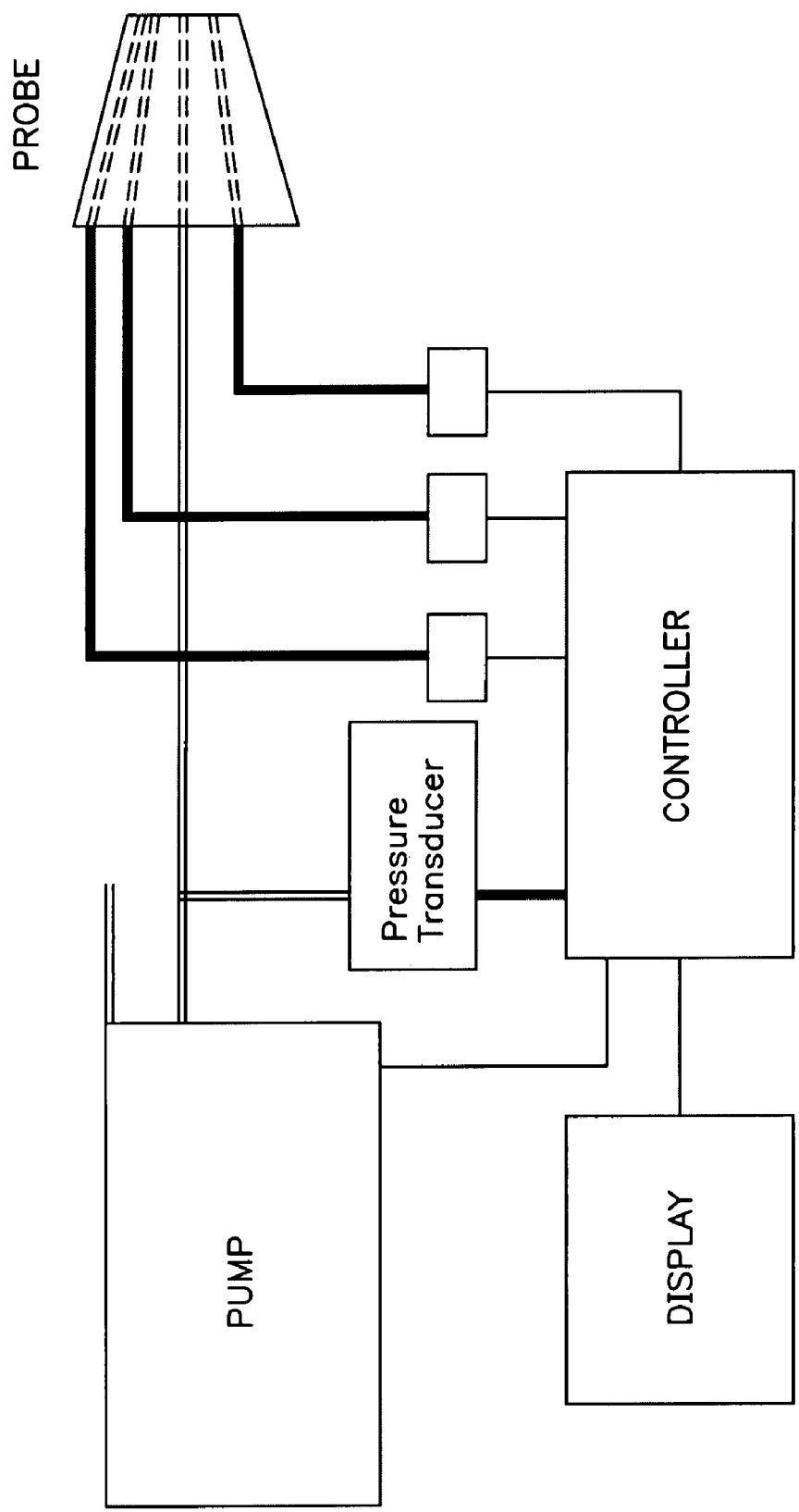
FIG. 4 is a schematic drawing showing a device according to the invention.

From FIG. 4 an audiological device incorporating a pump according to the invention is shown schematically. The device comprises a probe element adapted to be inserted into an ear canal of a person to be examined. A tubular element is at first end connected to a corresponding opening in the probe element and at second end opposite the first end connected to the opening 5, of the pump. A tubular element is at first end connected to the opening 5 of the pump housing by means of a T-shaped connecting branch and at second end connected to pressure transducer. The said pressure transducer provides an electrical signal for control electronics for the control of the pressure in the ear canal. Further tubular elements connects the outlet openings of sound output transducers to openings in the probe element and the inlet opening of a input transducer to an opening in the probe element. The output transducers are controlled by control electronics and the input transducer signal is delivered to a signal processor for further processing. In connection with the control electronics and the signal processor a control panel as well as output means, e.g. a display, are provided. The control electronics controls the opening and closing of the valve elements in relation to the piston movement in a manner that enables the creation of pressures above as well as below the surrounding atmospheric pressure. The piston movement is hereby also controlled by the control electronics. The different modes of operation where the pressures above and below the surrounding pressure are created may be part of an automated test procedure.

The operation of the pump in a situation where a pressure above the surrounding pressure is supplied to the ear canal takes place in the following manner.
1) The probe with the pressure tube from the pump is inserted into the ear canal.
2) The valve 5 is closed
3) The valve 4 is opened
4) The piston height is reduced by non-supply of electrical power
5) Air is drawn into the pump housing through valve 4
6) Valve 4 is closed
7) Valve 5 is opened
8) The piston height is increase by supply of electrical power and the air is supplied to the pressure tube
9) Repeating the steps 2-8 with the piston frequency selected The operation of the pump in a situation where a pressure below the surrounding pressure is supplied to the ear canal takes place in the following manner.
1) The probe with the pressure tube from the pump is inserted into the ear canal.
2) The valve 4 is closed
3) The valve 5 is opened
4) The piston height is reduced by non-supply of electrical power
5) Air is drawn into the pump housing through valve 5
6) Valve 5 is closed
7) Valve 4 is opened
8) The piston height is increase by supply of electrical power and the air is exited to the surroundings
9) Repeating the steps 2-8 with the piston frequency selected Such devices are used for providing audiological tests. One example of such test is the recording of a tympanogram. This test serves its purpose in evaluation of conductive hearing loss and assessment of middle ear function. After a number of initial procedures comprising instructing the patient and initializing the equipment the test procedure may be started. The probe is inserted in the ear canal to be tested. The probe should have an airtight sealing. During the test procedure the pressure is sweeped from a desired maximum pressure level to a desired minimum pressure level. During this pressure sweep the equipment generates a sound or tone signal through an output transducer, where this signal is reflected by the tympanic membrane and the reflected signal can be obtained by the input transducer adapted for this purpose. The values recorded may be displayed in a X-Y diagram.

The invention claimed is:

1. A measuring device for acoustic measurement in an ear canal, the device comprising a probe for insertion into an ear canal in a sealing manner and having an opening for transport of air into or out of the ear canal, and a pump for providing a pressure difference in relation to a surrounding atmospheric pressure, the pump comprising a housing with openings for inlet and/or outlet, one of said openings being operatively connected to the opening in the probe, a piston element having piezo electric properties within the housing, and valve elements having piezo electric properties controlling the inlet and outlet openings.

2. A measuring device according to claim 1, where the pump operates at a frequency above 18 kHz.

3. A measuring device according to claim 1, including control electronics for controlling valve positions in relation to the piston movement in such a manner that in one mode of operation a pressure above the surrounding pressure may be obtained and in another mode of operation is pressure below the surrounding pressure may be obtained.

4. A measuring device according to claim 1, including a pressure operated passive valve element in connection with pressurized parts of the device.

5. A measuring device according to claim 2, wherein said pump operates at a frequency above 20 kHz.

* * * * *